United States Patent
Wang et al.

(10) Patent No.: US 12,169,203 B2
(45) Date of Patent: Dec. 17, 2024

(54) NATIVE MICROFLUIDIC CE-MS ANALYSIS OF ANTIBODY CHARGE HETEROGENEITY

(71) Applicant: Regeneron Pharmaceuticals, Inc., Tarrytown, NY (US)

(72) Inventors: Hongxia Wang, Briarcliff Manor, NY (US); Haibo Qiu, Hartsdale, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 609 days.

(21) Appl. No.: 16/777,230

(22) Filed: Jan. 30, 2020

(65) Prior Publication Data

US 2020/0249241 A1 Aug. 6, 2020

Related U.S. Application Data

(60) Provisional application No. 62/799,331, filed on Jan. 31, 2019, provisional application No. 62/851,365, filed on May 22, 2019.

(51) Int. Cl.
*G01N 33/68* (2006.01)
*G01N 1/40* (2006.01)

(52) U.S. Cl.
CPC ....... *G01N 33/6848* (2013.01); *G01N 1/4044* (2013.01)

(58) Field of Classification Search
None
See application file for complete search history.

(56) References Cited

U.S. PATENT DOCUMENTS

2010/0187113 A1* 7/2010 Dolnik .................. B01D 57/02
204/453

OTHER PUBLICATIONS

Chames, P. et al. Bispecific antibodies for cancer therapy The light at the end of the tunnel? mAbs 1:6, 539-547; (Year: 2009).*
Redman, E.A. et al. Characterization of Intact Antibody Drug Conjugate Variants Using Microfluidic Capillary Electrophoresis—Mass Spectrometry, Analytical Chemistry, 2016, 88, 2220-2226 (Year: 2016).*
Francois, Y. et al. Characterization of cetuximab Fc/2 dimers by off-line CZE-MS, Analytica Chimica Acta 908 (2016) 168e176 (Year: 2016).*
C. Lew et al., "Rapid Level-3 Characterization of Therapeutic Antibodies by Capillary Electrophoresis Electrospray Ionization Mass Spectrometry," Journal of Chromatographic Science, vol. 53, No. 3, Feb. 13, 2015, pp. 443-449.

(Continued)

*Primary Examiner* — Xiaoyun R Xu
(74) *Attorney, Agent, or Firm* — Kramer Levin Naftalis & Frankel LLP

(57) ABSTRACT

Methods for detecting and/or discriminating between post-translational modification variants of an antibody of interest in a sample. The methods including: contacting a sample comprising one or more antibodies of interest with a protease to digest the sample into antibody fragments; separating antibody fragments by molecular weight and/or charge in one or more capillaries using capillary electrophoresis; eluting separated antibody fragments from the one or more capillaries; and determining the mass of the eluted antibody fragments by mass spec analysis, thereby detecting and/or discriminating between post-translational modification variants of the antibody of interest.

20 Claims, 14 Drawing Sheets

Specification includes a Sequence Listing.

(56) References Cited

OTHER PUBLICATIONS

Said Nassur et al., "Structural characterization of antibody drug conjugate by a combination of intact, middle-up and bottom-up techniques using sheathless capillary electrophoresis—Tandem mass spectrometry as nanoESI infusion platform and separation method," Analytica Chimica Acta, Elsevier, Amsterdam, NL, vol. 918, Mar. 18, 2016, pp. 50-59.

Rob Haselberg et al., "Heterogeneity assessment of antibody-derived therapeutics at the intact and middle-up level by low-flow sheathless capillary electrophoresis-mass spectrometry," Analytica Chimica Acta, vol. 1044, Dec. 1, 2018, pp. 181-190.

Ihan Mei et al., "Intact mass analysis of monoclonal antibodies by capillary electrophoresis—Mass spectrometry." Journal of Chromatography B: Biomedical Sciences & Applications, Elsevier, Amsterdam, NL, vol. 1011, Dec. 28, 2015, pp. 24-32.

International Search Report PCT Application No. PCT/US2020/015875, International Filing Date Jan. 30, 2020, Date of Mailing May 29, 2020.

Chen et al: "Quick screening of intact antibody and antibody drug conjugates with integrated microfluidic capillary electrophoresis and mass spectrometry",Jan. 1, 2017 (Jan. 1, 2017), pp. 1-9, XP055982137, Retrieved from the Internet: URL:https://908devices.com/wp-content/uploads/2021/11/ZipChip_AppNote_Thermo-Quick-Screening.pdf.

Khatri Kshitij et al: "Microfluidic Capillary Electrophoresis-Mass Spectrometry for Analysis of Monosaccharides, Oligosaccharides, and Glycopeptides",Analytical Chemistry, vol. 89, No. 12, Jun. 6, 2017 (Jun. 6, 2017), pp. 6645-6655, XP055982431,US, ISSN: 0003-2700, DOI: 10.1021/acs.analchem.7b00875, Retrieved from the Internet: URL:https://pubs.acs.org/doi/pdf/10.1021/acs.analchem.7b00875.

Williamson, A. "ZipChip™ and Thermo Scientific™ MS for CE/ESI-MS Analyses," ThermoFisher Scientific, retrieved from [Online] https://www.pragolab.cz/files/clanky/2018-02/ZipChip%20Presentation.pdf. 2018. p. 1-31.

\* cited by examiner

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Enzymatically produced peptide

<400> SEQUENCE: 1

Pro Lys Ser Cys Asp Lys Thr His Thr Cys Pro Pro Cys Pro
1               5                   10

NATIVE MICROFLUIDIC CE-MS ANALYSIS OF ANTIBODY CHARGE HETEROGENEITY

REFERENCE TO A SEQUENCE LISTING

This application incorporates by reference the Sequence Listing submitted in Computer Readable Form as file 10553P2-US_Sequence.txt, created on May 22, 2019 and containing 487 bytes.

FIELD OF THE INVENTION

The present invention pertains to biopharmaceuticals, and relates to the use of capillary electrophoresis and mass spectral analysis to detect in vitro and/or in vivo post-translational modifications of therapeutic antibodies.

BACKGROUND

Monoclonal antibodies (mAbs) are a significant class of biotherapeutic products, and they have achieved outstanding success in treating many life-threatening and chronic diseases. However, in certain circumstances therapeutic monoclonal antibodies (mAbs) are heterogeneous molecules produced in mammalian cells with many product variants, including variants resulting from post-translational modifications (PTMs). Variants produced via PTMs can occur throughout the lifespan of a mAb during production, purification, storage, and post-administration. These variants or product-related modifications are also referred to as product quality attributes (PQAs). Controlling PQAs within pre-defined acceptance criteria is vital to the biopharmaceutical industry because it ensures consistent product quality and reduces potential impacts on drug safety and efficacy.

Each individual monoclonal antibody may therefore present a unique profile, a characteristic which needs to be taken into consideration during the evaluation of these products both during development and manufacturing of final product. A Food and Drug Administration guidance for industry recommends that sponsors should evaluate susceptibilities of therapeutic proteins to modifications within the in vivo milieu (see, Guidance for Industry, Immunogenicity Assessment for Therapeutic Protein Products. 2014). As a result, in vitro and/or in vivo behavior of many PQAs, including deamidation (see, for example, Huang et al., Analytical chemistry 2005; 77:1432-9; Ouellette et al., mAbs 2013; 5:432-44; Yin et al., Pharmaceutical research 2013; 30:167-78; Li et al., mAbs 2016:0; Li et al., mAbs 2016:0), oxidation (see, for example, Yin et al., Pharmaceutical research 2013; 30:167-78; Li et al., mAbs 2016:0; Li et al., mAbs 2016:0), glycation (see, for example, Goetze et al., Glycobiology 2012; 22:221-34), glycosylation (see, for example, Li et al., mAbs 2016:0; Li et al., mAbs 2016:0; Goetze et al., Glycobiology 2011; 21:949-59; Alessandri et al., mAbs 2012; 4:509-20.), disulfides (see, for example, Li Yet al., mAbs 2016:0; Liu et al., The Journal of biological chemistry 2008; 283:29266-72), N-terminal pyroglutamate (see, for example, Yin et al., Pharmaceutical research 2013; 30:167-78; Li et al., mAbs 2016:0; Li et al., mAbs 2016:0; Liu et al., The Journal of biological chemistry 2011; 286:11211-7), and C-terminal lysine removal (see, for example, Li et al., mAbs 2016:0; Cai et al., Biotechnology and bioengineering 2011; 108:404-12) have been investigated in animal or human samples. Accordingly, additional methods of monitoring mAb preparations are needed.

SUMMARY OF THE INVENTION

In one aspect, the present invention provides a method for detecting and/or discriminating between post-translational modification variants of an antibody of interest in a sample, in which the method includes: contacting a sample comprising one or more antibodies of interest with a protease to digest the sample into antibody fragments; separating antibody fragments by molecular weight and/or charge in one or more capillaries using capillary electrophoresis; eluting separated antibody fragments from the one or more capillaries; and determining the mass of the eluted antibody fragments by mass spec analysis, thereby detecting and/or discriminating between post-translational modification variants of the antibody of interest.

In various embodiments of the method, the post-translational modification comprises one or more of deamidation, oxidation, glycation, disulfide formation, N-terminal pyroglutamate formation, C-terminal lysine removal, and high mannose glycosylation.

In various embodiments of the method, the protease comprises IdeS.

In various embodiments of the method, the antibody fragments comprise one or more of an $F(ab')_2$ or Fc antibody subunit.

In various embodiments of the method, the antibody of interest is a mAb.

In various embodiments of the method, the antibody fragments are separated by charge and the method is a method of detecting and/or discriminating between charge variants of the antibody of interest.

In various embodiments of the method, the antibody fragments are separated by molecular weight and the method is a method of detecting and/or discriminating between size variants of the antibody of interest.

In some embodiments, the method further includes determining a relative or absolute amount of the post-translational modification variants of an antibody of interest in a sample.

In various embodiments of the method, the antibody of interest comprises a bispecific antibody.

In various embodiments of the method, the sample includes an internal standard.

In various embodiments of the method, the one or more capillaries comprise a separation matrix.

In various embodiments of the method, the separation matrix comprises a sieving matrix configured to separate proteins by molecular weight.

In various embodiments of the method, eluting separated antibody fragments from the one or more capillaries further comprises separating the antibody fragments into one or more fractions.

In some embodiments, the method further includes identifying the antibody fragments.

In some embodiments, the method further includes identifying the post-translational modification present on the antibody fragments.

In various embodiments of the method, the monoclonal antibody of interest is of isotype IgG1, IgG2, IgG3, IgG4, or mixed isotype.

In some embodiments, the method further includes post-translational modification profiling of the antibody of interest.

In some embodiments, the method further includes post-translational modification mapping of post-translational modification hotspots by reduced peptide mapping LC-MS/MS analysis.

In various embodiments of the method, the sample comprises a mixture of antibodies of interest.

In various embodiments of the method, the monoclonal antibody of interest is an antibody drug conjugate.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

DETAILED DESCRIPTION OF THE INVENTION

Figure 1:
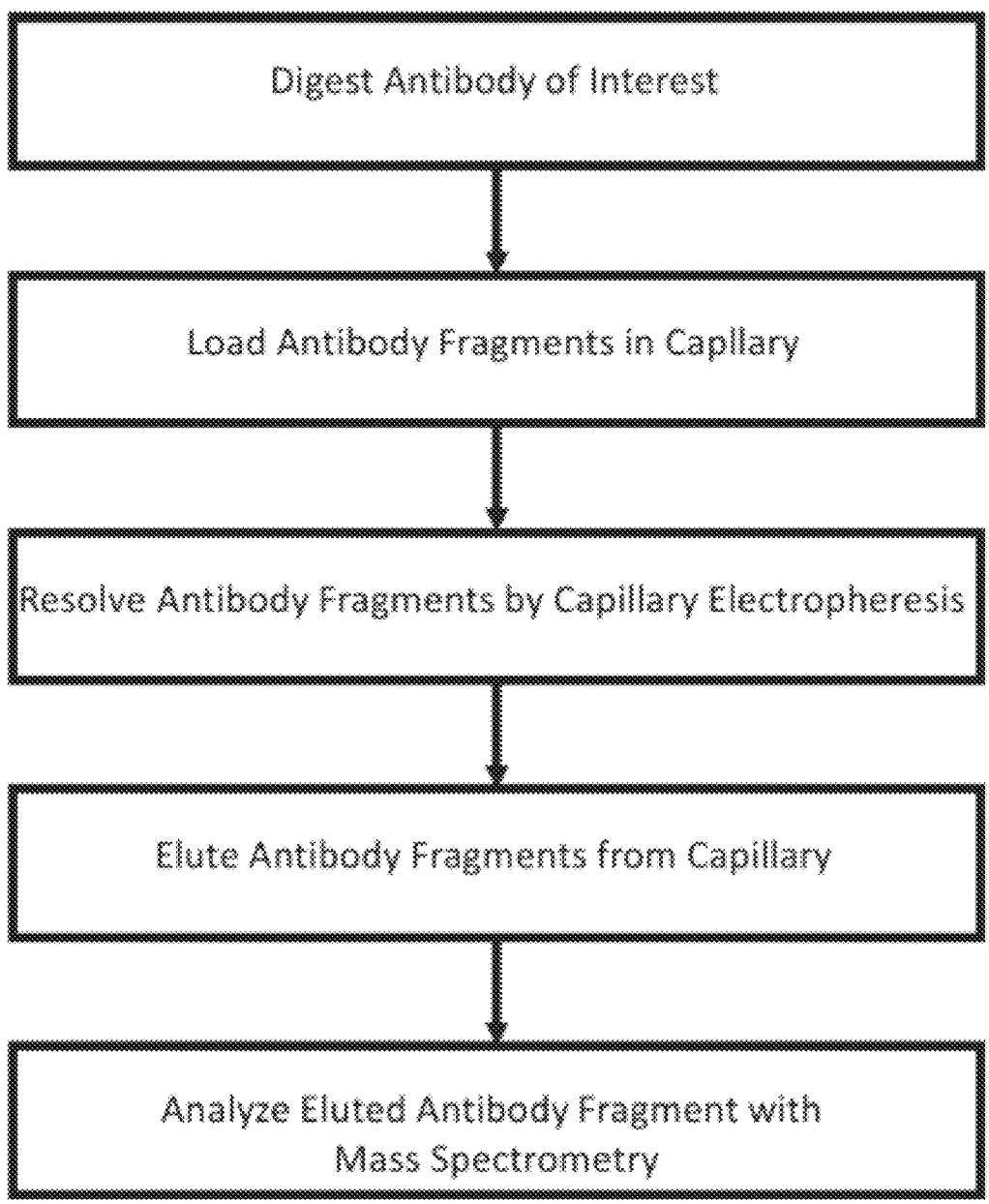
FIG. 1 is a diagram of an exemplary work flow for the separation and detection of post-translational modified antibody fragments by capillary electrophoresis and mass spectral analysis.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

ABBREVIATIONS USED HEREIN mAb: Monoclonal antibody
biAb: Bispecific antibody
CQA: Critical quality attributes
CE: Capillary Electrophoresis
PTM: Post-Translational Modification Variant
IEC: Ion Exchange Chromatography
UV: Ultra Violet
QC: Quality Control
MS: Mass Spec
ADC: Antibody Drug Conjugate The term "antibody", as used herein, is intended to refer to immunoglobulin molecules included of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is included of a heavy chain variable region ("HCVR" or "$V_H$") and a heavy chain constant region (included of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is included of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains,* 27(1) Dev. Comp. Immunol. 55-77 (2003); and M. Potter, *Structural correlates of immunoglobulin diversity,* 2(1) Surv. Immunol. Res. 27-42 (1983).

The term antibody also encompasses a "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527(Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al.

(1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989).

The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "ADC" or "antibody-drug conjugate" refers to an antibody or antigen-binding fragment thereof conjugated to a therapeutic moiety such as a cytotoxic agent, a chemotherapeutic drug, immunosuppressant or a radioisotope. Cytotoxic agents include any agent that is detrimental to the growth, viability or propagation of cells. Examples of suitable cytotoxic agents and chemotherapeutic agents for forming ADCs are known in the art.

The term "sample," as used herein, refers to a mixture of molecules that includes at least one polypeptide of interest, such as a monoclonal antibody or a bispecific antibody or fragment thereof, that is subjected to manipulation in accordance with the methods of the invention, including, for example, separating, analyzing, extracting, concentrating or profiling.

The terms "analysis" or "analyzing," as used herein, are used interchangeably and refer to any of the various methods of separating, detecting, isolating, purifying, solubilizing, detecting and/or characterizing molecules of interest (e.g., polypeptides, such as antibodies) and contaminants in antibody preparations. Examples include, but are not limited to, electrophoresis, mass spectrometry, e.g., tandem mass spectrometry, ultraviolet detection, and combinations thereof.

"Chromatography," as used herein, refers to the process of separating a mixture, for example a mixture containing peptides, proteins, polypeptides and/or antibodies, such as monoclonal antibodies. It involves passing a mixture through a stationary phase, which separates molecules of interest from other molecules in the mixture and allows one or more molecules of interest to be isolated. In the method disclosed herein chromatography refers to capillary electrophoresis, including size based capillary electrophoresis and isoelectric focusing or charged based capillary electrophoresis.

The term "isolated," as used herein, refers to a biological component (such as an antibody, for example a monoclonal antibody) that has been substantially separated, produced apart from, or purified away from other biological components in the cell of the organism in which the component naturally occurs or is transgenically expressed, that is, other chromosomal and extrachromosomal DNA and RNA, proteins, lipids, and metabolites. Nucleic acids, peptides, proteins, lipids and metabolites which have been "isolated" thus include nucleic acids, peptides, proteins, lipids, and metabolites purified by standard or non-standard purification methods. The term also embraces nucleic acids, peptides, proteins, lipids, and metabolites prepared by recombinant expression in a host cell as well as chemically synthesized peptides, lipids, metabolites, and nucleic acids.

The terms "peptide," "protein" and "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine I He; Lysine K Lys; Leucine L Leu; Methionine M Met; Asparagine N Asn; Proline P Pro; Glutamine Q Gln; Arginine R Arg; Serine S Ser; Threonine T Thr; Valine V Val; Tryptophan w Trp; and Tyrosine Y Tyr. In one embodiment a peptide is an antibody or fragment or part thereof, for example, any of the fragments or antibody chains listed above. In some embodiments, the peptide may be post-translationally modified. As used herein, the terms "protein of interest" and/or "target protein of interest" refer to any protein to be separated and/or detected with the methods, provided herein. Suitable protein of interests include antibodies, for example monoclonal antibodies, and fragments thereof.

"Detect" and "detection" have their standard meaning, and are intended to encompass detection including the presence or absence, measurement, and/or characterization of a protein of interest, such as a mAb or fragment thereof.

As used herein, the terms "standard" and/or "internal standard" refer to a well-characterized substance of known amount and/or identity (e.g., known molecular weight, electrophoretic mobility profile) that can be added to a sample and both the standard and the molecules in the sample, on the basis of molecular weight or isoelectric point by electrophoresis). A comparison of the standard then provides a quantitative or semi-quantitative measure of the amount of analyte, such as mAb or fragments thereof present in the sample.

"Contacting," as used herein, includes bringing together at least two substances in solution or solid phase, for example contacting a sample with an enzyme, such as a protease.

The term "corresponding" is a relative term indicating similarity in position, purpose or structure, and may include peptides of identical structure but for the presence or absence of a post-translational modification. In some embodiments, mass spectral signals in a mass spectrum that are due to corresponding peptides of identical structure but for the presence or absence of a post-translational modification are "corresponding" mass spectral signals. A mass spectral signal due to a particular peptide is also referred to as a signal corresponding to the peptide. In certain embodiments, a particular peptide sequence or set of amino acids can be assigned to a corresponding peptide mass.

The terms "fragment peptide" or "peptide fragment," as used herein, refer to a peptide that is derived from the full length polypeptide, such as a protein and/or monoclonal antibody, through processes including fragmentation, enzymatic proteolysis, or chemical hydrolysis. Such proteolytic peptides include peptides produced by treatment of a protein with one or more proteases such as IdeS protease. A fragment peptide, or peptide fragment, can be a digested peptide.

"Mass spectrometry" refers to a method in which a sample is analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), orbitrap mass analyzer, Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example, one or more dimensions of liquid or size exclusion chromatography.

Tandem mass spectrometry or MS/MS is a technique to break down selected ions (precursor ions) into fragments (product ions). The fragments then reveal aspects of the chemical structure of the precursor ion. In tandem mass spectrometry, once samples are ionized (for example by ESI, MALDI, EI, etc.) to generate a mixture of ions, precursor ions, for example peptides from a digest of a specific mass-to-charge ratio (m/z) are selected (MS1) and then fragmented (MS2) to generate a product ions for detection. Typical Tandem MS instruments include QqQ, QTOF, and hybrid ion trap/FTMS, etc. One example of an application of tandem mass spectrometry is protein identification. The first mass analyzer isolates ions of a particular m/z value that represent a single species of peptide among many introduced into and then emerging from the ion source. Those ions are then accelerated into a collision cell containing an inert gas such as argon to induce ion fragmentation. This process is designated collisionally induced dissociation (CID) or collisionally activated dissociation (CAD). The m/z values of fragment ions are then measured in a $2^{nd}$ mass analyzer to obtain amino acid sequence information.

References to a mass of an amino acid mean the monoisotopic mass or average mass of an amino acid at a given isotopic abundance, such as a natural abundance. In some examples, the mass of an amino acid can be skewed, for example, by labeling an amino acid with an isotope. Some degree of variability around the average mass of an amino acid is expected for individual single amino acids based on the exact isotopic composition of the amino acid. The masses, including monoisotopic and average masses for amino acids are easily obtainable by one of ordinary skill the art.

Similarly, references to a mass of a peptide means the monoisotopic mass or average mass of a peptide at a given isotopic abundance, such as a natural abundance. In some examples, the mass of a peptide can be skewed, for example, by labeling one or more amino acids in the peptide with an isotope. Some degree of variability around the average mass of a peptide is expected for individual single peptides based on the exact isotopic composition of the peptide. The mass of a particular peptide can be determined by one of ordinary skill the art.

General Description

Characterization of monoclonal antibody (mAb) variants is important in order to identify their potential impact on safety, potency, and stability of a potential therapeutic antibody. For example, to be considered for approval by regulatory agencies, extensive characterization of the molecule must be performed. In drug products comprising mixtures of antibodies, characterization of the absolute or relative amounts of each antibody must be determined. Because aggregates and fragments may potentially affect immunogenicity and potency, their levels are typically monitored during lot release, stability, and characterization. Furthermore, primary degradation pathways for the molecule and product related impurities and variants are determined. Ion exchange chromatography (IEC) coupled with UV detection is frequently used to separate and quantify mAb variants in routine quality control (QC). However, characterization of the chromatographic peaks resulting from an IEC separation is an extremely time-consuming process. Thus, additional methods are needed to characterize potential therapeutic mAbs and mAb preparations. The methods disclosed herein meet those needs.

Disclosed herein is a method for detecting and/or discriminating between variants of an antibody of interest, such as a monoclonal antibody (mAb), in a sample by a physical parameter, such as mass and/or charge. The inventors have developed a high-throughput and highly sensitive native microfluidic capillary electrophoresis (CE)-MS method for the quick identification of antibody charge variants for forced degradation and long-term stability studies.

Compared with IEC methods, high resolution and comparable charge profiles are obtained by the native microfluidic CE-MS. The disclosed methods can be used in QC evaluation of antibody preparations. In embodiments of the method, a sample that includes an antibody of interest is resolved or separated by using capillary electrophoresis, for example on one or more capillaries of a CE-system. In certain embodiments, the sample is resolved or separated by molecular weight and charge. For example, using separation by mass and charge or m/z ratio fragments with the same mass but different charges can be resolved. Similarly, using separation by mass and charge or m/z ratio fragments with the same change but different masses can be resolved. In embodiments, the method includes liberating fragments of an antibody of interest, such as a monoclonal antibody (mAb), for example by contacting the sample comprising one or more antibodies of interest with a protease to digest the sample. In an embodiment, the protease is IdeS protease. Once digestion, either partial or full, is conducted, antibody fragments can be separated by molecular weight and/or charge in one or more capillaries using capillary electrophoresis. The separated antibody fragments can be eluted from the one or more capillaries and the mass of the eluted antibody fragments determined by mass spec analysis to detect and/or discriminate between post-translational modification variants of the antibody of interest, for example by detection and/or determination of the PTM profile of the fragments of the antibody of interest. In certain embodiments, the antibody fragments include one or more of an F(ab')$_2$ or Fc antibody subunit, for example as digested from the intact antibody using a protease, such as the IdeS protease. In certain embodiments, the antibody of interest is a monoclonal antibody, such as a currently used therapeutic antibody or one undergoing evaluation, including novel monoclonal antibodies. In certain embodiments, the monoclonal antibody of interest is part of an antibody drug conjugate (ADC). In certain embodiments, the antibody fragments are separated by charge and the method is a method of detecting and/or discriminating between charge variants of the antibody of interest. In certain embodiments, the antibody fragments are separated by molecular weight and the method is a method of detecting and/or discriminating between size variants of the antibody of interest. In certain embodiments, the antibody fragments are separated by charge and molecular weight and the method is a method of detecting and/or discriminating between charge and molecular weight variants of the antibody of interest. In certain embodiments, the method includes determining a relative or absolute amount of the post-translational modification variants of an antibody of interest in a sample, for example from the antibody fragments.

As noted above, separation of the antibody fragments by mass and charge has the benefit of being able to determine the homogeneity of the antibody fragments, for example, changes in surface charge of the antibody that may not be easily seen in separation by just molecular weight. This separation allows for the determination of the type and level of post-translational modification on the fragments in the sample. The presence of post-translational modifications (PTMs) on a monoclonal antibody (mAb) induces charge heterogeneity (see Table 1) and potentially affects drug stability and biological activity. Therefore, monitoring the PTMs and associated charge variant profiles of mAbs during drug development is important. Here, we present the development of a high-throughput and highly sensitive native microfluidic CE-MS method for the quick identification of mAb charge variants and its application to forced degradation and long-term stability studies. Relative to ion exchange chromatography (IEX) based approaches, high resolution with comparable charge variant profiles can be obtained using the native microfluidic CE-MS method as disclosed herein.

TABLE 1

Source of Antibody Charge Heterogeneity

| Major PTMs/Degradation Pathway | Effect | Species Formed |
|---|---|---|
| Sialylation | COOH addition | Acidic |
| Deamidation | COOH formation | Acidic |
| C-terminal lysine cleavage | Loss of NH2 | Acidic |
| Adduct formation | COOH formation or loss of NH2 | Acidic |
| Succinimide formation | Loss of COOH | Basic |
| Methionine, cysteine, lysine, histidine, tryptophan oxidation | Conformational change | Basic |
| Disulfide-mediated | Conformational change | Basic |
| Asialylation (terminal Galactose) | Loss of COOH | Basic |
| C-terminal lysine and glycine amidation | NH2 formation or loss of COOH | Basic |

In certain embodiments, the post-translational modification is one or more of deamidation, oxidation, glycation, disulfide formation, N-terminal pyroglutamate formation, C-terminal lysine removal, and high mannose glycosylation.

In certain embodiments, the sample is resolved or separated within a single capillary. In certain embodiments, the sample is resolved or separated within multiple capillaries, for example in parallel. By way of example with respect to separation by molecular weight, the smaller the fragment of an antibody, the further within a capillary it would be expected to travel over a given period of time. In addition, one would expect differences in the charge of antibody fragments to be subjected to different travel times depending on the charge.

In embodiments, the sample may contain multiple, such as at least 2, at least 3, at least 4, at least 5 or more sets of antibody fragments from multiple antibodies of interest. In some embodiments, the method further includes determining a relative or absolute amount of the variants of the antibody fragments in a sample, for example by measurement of peak height or area, which corresponds to the amount of antibody fragment in the sample. In some embodiments, the antibody of interest comprises a bispecific monoclonal antibody. In some embodiments, the sample includes one or more internal standards, for example a ladder of molecular weight standards, a ladder of isoelectric point standards, or even a standard used as a baseline or benchmark for determining the amount of an antibody fragments of interest in the sample.

The ability to discriminate between mAbs in an mAb cocktail of multiple mAbs is becoming increasingly important as these multiple component therapies demonstrate increased efficacy in disease treatment. Thus, improved methods of monitoring how the individual mAbs behave in these systems will become increasingly important in the assessment of the compatibility and stability of these multi-mAb therapies. To meet this growing need this disclosure provides a method for detecting and/or discriminating between monoclonal antibodies in a mixture of two of more monoclonal antibodies in a sample.

In embodiments, the method includes separating protein components of a sample with two or more mAbs of interest, such as 2, 3, 4, 5, 6, 7, 8, 9 10 or even more, mAbs of interest, by charge in one or more capillaries using capillary electrophoresis In some embodiments, a charge based profile or fingerprint of the antibody of interest can be created, for example of the antibody of interest alone for comparison with a charge based profile or fingerprint of the antibody in the mixture, for example a charge based profile or fingerprint corresponding to the post-translational modification. This comparison can then be used to determine if the antibody of interest changes in the mixture. This profile or fingerprint comparison can be done for any or all of the antibodies of interest in the mixture.

Samples for use in the disclosed methods can be heterogeneous, containing a variety of components, i.e. different proteins. Alternatively, the sample can be homogenous, containing one component or essentially one component of multiple charge or molecular weight species. Pre-analysis processing may be performed on the sample prior to detecting the antibody of interest, such as a mAb or multiple mAbs. For example, the sample can be subjected to a lysing step, denaturation step, heating step, purification step, precipitation step, immunoprecipitation step, column chromatography step, centrifugation, etc. In some embodiments, the separation of the sample and immobilization may be performed on native substrates. In other embodiments, the sample may be subjected to denaturation, for example, heat and/or contact with a denaturizing agent. Denaturizing agents are known in the art. In some embodiments, the sample may be subjected to non-reducing conditions. In some embodiments, the sample may be subjected to reducing conditions, for example, by contacting the sample with one or more reducing agents. Reducing agents are knowns in the art.

In embodiments, the capillary may include a separation matrix, which can be added in an automated fashion by the apparatus and/or system. In some embodiments, the sample is loaded onto a stacker matrix prior to separation. The separation matrix, in one embodiment, is a size separation matrix, and has similar or substantially the same properties of a polymeric gel, used in conventional electrophoresis techniques. Capillary electrophoresis in the separation matrix is analogous to separation in a polymeric gel, such as a polyacrylamide gel or an agarose gel, where molecules are separated on the basis of the size of the molecules in the sample, by providing a porous passageway through which the molecules can travel. The separation matrix permits the separation of molecules by molecular size because larger molecules will travel more slowly through the matrix than smaller molecules. In some embodiments, the one or more capillaries comprise a separation matrix. In some embodiments, the sample containing an antibody of interest is separated or resolved based on molecular weight. In some embodiments, the separation matrix comprises a sieving matrix configured to separate proteins by molecular weight. In some embodiments, protein components of a sample are separated by molecular weight and the method is a method of detecting and/or discriminating between size variants of an antibody of interest. In some embodiments, antibody fragments of a sample are separated by molecular weight and the method is a method of detecting and/or discriminating between size variants of a contaminating protein of interest.

A wide variety of solid phase substrates are known in the art, for example gels, such as polyacrylamide gel. In some embodiments, resolving one or more proteins of interest includes electrophoresis of a sample in a polymeric gel. Electrophoresis in a polymeric gel, such as a polyacrylamide gel or an agarose gel separates molecules on the basis of the molecule's size. A polymeric gel provides a porous passageway through which the molecules can travel. Polymeric gels permit the separation of molecules by molecular size because larger molecules will travel more slowly through the gel than smaller molecules.

In some embodiments, the sample containing a protein of interest is separated or resolved based on the charge of the components of the sample. In some embodiments, protein components of a sample are separated by charge and the method is a method of detecting and/or discriminating between charge variants of a monoclonal antibody of interest. In some embodiments, fragments of a sample are separated by charge and the method is a method of detecting and/or discriminating between charge variants of an antibody of interest.

In some embodiments, an internal standard can be a purified form of the antibody of interest itself or fragment thereof, which is generally made distinguishable from the antibody of interest in some way. Methods of obtaining a purified form of the antibody of interest itself or fragment thereof can include, but are not limited to, purification from nature, purification from organisms grown in the laboratory (e.g., via chemical synthesis), and/or the like. The distinguishing characteristic of an internal standard can be any suitable change that can include, but is not limited to, dye labeling, radiolabeling, or modifying the mobility of the standard during the electrophoretic separation so that it is separated from the antibody of interest. For example, a standard can contain a modification of the antibody of interest itself or fragment thereof that changes the charge, mass, and/or length (e.g., via deletion, fusion, and/or chemical modification) of the standard relative to the antibody of interest itself or fragment thereof. Thus, the antibody of interest itself or fragment thereof and the internal standard can each be labeled with fluorescent dyes that are each detectable at discrete emission wavelengths, thereby allowing the protein of interest and the standard to be independently detectable. In some instances, an internal standard is different from the antibody of interest itself or fragment thereof but behaves in a way similar to or the same as the antibody of interest itself or fragment thereof, enabling relevant comparative measurements.

As will be appreciated by those in the art, virtually any method of loading the sample in the capillary may be performed. For example, the sample can be loaded into one end of the capillary. In some embodiments, the sample is loaded into one end of the capillary by hydrodynamic flow. For example, in embodiments wherein the fluid path is a capillary, the sample can be loaded into one end of the capillary by hydrodynamic flow, such that the capillary is used as a micropipette. In some embodiments, the sample can be loaded into the capillary by electrophoresis, for example, when the capillary is gel filled and therefore more resistant to hydrodynamic flow.

The capillary can include any structure that allows liquid or dissolved molecules to flow. Thus, the capillary can include any structure known in the art, so long as it is compatible with the methods. In some embodiments, the capillary is a bore or channel through which a liquid or dissolved molecule can flow. In some embodiments, the capillary is a passage in a permeable material in which liquids or dissolved molecules can flow.

The capillary includes any material that allows the detection of the protein of interest within the capillary. The capillary includes any convenient material, such as glass, plastic, silicon, fused silica, gel, or the like. In some embodiments, the method employs a plurality of capillaries. A plurality of capillaries enables multiple samples to be analyzed simultaneously.

The capillary can vary as to dimensions, width, depth and cross-section, as well as shape, being rounded, trapezoidal, rectangular, etc., for example. The capillary can be straight, rounded, serpentine, or the like. As described below, the length of the fluid path depends in part on factors such as sample size and the extent of sample separation required to resolve the protein of interest.

In some embodiments, the capillary includes a tube with a bore. In some embodiments, the method employs a plurality of capillaries. Suitable sizes include, but are not limited to, capillaries having internal diameters of about 10 to about 1000 µm, although more typically capillaries having internal diameters of about 25 to about 400 µm can be utilized. Smaller diameter capillaries use relatively low sample loads while the use of relatively large bore capillaries allows relatively high sample loads and can result in improved signal detection.

The capillaries can have varying lengths. Suitable lengths include, but are not limited to, capillaries of about 1 to 20 cm in length, although somewhat shorter and longer capillaries can be used. In some embodiments, the capillary is about 1, 2, 3, 4, 5, or 6 cms in length. Longer capillaries typically result in better separations and improved resolution of complex mixtures. Longer capillaries can be of particular use in resolving low abundance proteins of interest.

Generally, the capillaries are composed of fused silica, although plastic capillaries and PYREX (i.e., amorphous glass) can be utilized. As noted above, the capillaries do not need to have a round or tubular shape. Other shapes, so long as they are compatible with the methods described herein, may also be used.

In some embodiments, the capillary can be a channel. In some embodiments, the method employs a plurality of channels. In some embodiments, the capillary can be a channel in a microfluidic device. Microfluidics employ channels in a substrate to perform a wide variety of operations. The microfluidic devices can include one or a plurality of channels contoured into a surface of a substrate. The microfluidic device can be obtained from a solid inert substrate, and in some embodiments in the form of a chip. The dimensions of the microfluidic device are not critical, but in some embodiments the dimensions are on the order of about 100 µm to about 5 mm thick and approximately about 1 centimeter to about 20 centimeters on a side. Suitable sizes include, but are not limited to, channels having a depth of about 5 µm to about 200 µm, although more typically having a depth of about 20 µm to about 50 µm can be utilized. Smaller channels, such as micro or nanochannels can also be used, so long as they are compatible with the methods.

The antibody fragments may be obtained from an antibody of interest, such as a monoclonal antibody. The antibody fragments may be prepared by reduction, enzymatic digestion, denaturation, fragmentation, chemical cleavage or a combination thereof. The methods disclosed herein are applicable to any antibody isotype, such as IgG1, IgG2, IgG3, IgG4, or mixed isotype.

Reduction is to reduce disulfide bonds into two thiols in a 3-dimensional protein, such as a monoclonal antibody. Reduction can be performed by heat-denaturing, adding a surfactant, or adding a denaturing agent, e.g., guanidine HCl (6M), in the presence of a reducing agent, e.g. TCEP-HCl. Enzymatic degradation is a digestion of the protein with a protease, e.g., trypsin or Achromobacter protease I (Lys-C). In addition, the glycoprotein can be denatured by heat or chemicals, or a combination thereof. Fragmentation involves cleaving protein portions of a single or multi-subunit protein, such as a monoclonal antibody, with physical, biological or chemical methods. For example, an immunoglobulin degrading enzyme from S. pyogenes (IdeS) is commonly used for antibody subunit fragmentation.

In various embodiments, an antibody in a sample can be treated and prepared by reduction, enzymatic degradation, denaturation or fragmentation prior to contacting with the hydrophilic enrichment substrate. The methods provide a novel chromatographic method to characterize the post-translational modification of antibodies, e.g., monoclonal antibody (mAb) therapeutics, by means of fragments. In certain embodiments, the samples at any intervening step may be concentrated, desalted or the like.

In some embodiments, the methods further comprise detecting the post-translationally modified antibody fragments, for example using the UV signal from the peptide portion of the post-translationally modified antibody fragments. This may be done for fractions of a sample and allows the selection of specific fractions for further analysis, for example mass spec (MS) analysis. Thus, in further embodiments, the detection step comprises mass spectroscopy or liquid chromatography-mass spectroscopy (LC-MS). In applications of mass spectrometry for the analysis of biomolecules, the molecules are transferred from the liquid or solid phases to gas phase and to vacuum phase. Since many biomolecules are both large and fragile (proteins being a prime example), two of the most effective methods for their transfer to the vacuum phase are matrix-assisted laser desorption ionization (MALDI) or electrospray ionization (ESI). Aspects of the use of these methods, and sample preparation requirements, are known to those of ordinary skill in the art. In general, ESI is more sensitive, while MALDI is faster. Significantly, some peptides ionize better in MALDI mode than ESI, and vice versa (Genome Technology, June 220, p 52). The extraction channel methods and devices of the instant invention are particularly suited to preparing samples for MS analysis, especially biomolecule samples such as post-translationally modified antibody fragments. An important advantage of the invention is that it allows for the preparation of an enriched sample that can be directly analyzed, without the need for intervening process steps, e.g., concentration or desalting.

ESI is performed by mixing the sample with volatile acid and organic solvent and infusing it through a conductive needle charged with high voltage. The charged droplets that are sprayed (or ejected) from the needle end are directed into the mass spectrometer, and are dried up by heat and vacuum as they fly in. After the drops dry, the remaining charged molecules are directed by electromagnetic lenses into the mass detector and mass analyzed. In one embodiment, the eluted sample is deposited directly from the capillary into an electrospray nozzle, e.g., the capillary functions as the sample loader. In another embodiment, the capillary itself functions as both the extraction device and the electrospray nozzle.

For MALDI, the analyte molecules (e.g., proteins) are deposited on metal targets and co-crystallized with an organic matrix. The samples are dried and inserted into the mass spectrometer, and typically analyzed via time-of-flight (TOF) detection. In one embodiment, the eluted sample is deposited directly from the capillary onto the metal target, e.g., the capillary itself functions as the sample loader. In one embodiment, the extracted analyte is deposited on a MALDI target, a MALDI ionization matrix is added, and the sample is ionized and analyzed, e.g., by TOF detection.

In some embodiments, other ionization modes are used e.g. ESI-MS, turbospray ionization mass spectrometry, nanospray ionization mass spectrometry, thermospray ionization mass spectrometry, sonic spray ionization mass spectrometry, SELDI-MS and MALDI-MS. In general, an advantage of these methods is that they allow for the "just-in-time" purification of sample and direct introduction into the ionizing environment. It is important to note that the various ionization and detection modes introduce their own constraints on the nature of the desorption solution used, and it is important that the desorption solution be compatible with both. For example, the sample matrix in many applications must have low ionic strength, or reside within a particular pH range, etc. In ESI, salt in the sample can prevent detection by lowering the ionization or by clogging the nozzle. This problem is addressed by presenting the analyte in low salt and/or by the use of a volatile salt. In the case of MALDI, the analyte should be in a solvent compatible with spotting on the target and with the ionization matrix employed. In embodiments, the method further includes identifying the antibody fragments, for example the sequence of the antibody fragments. In embodiments, the method further includes identifying the post-translational modification present on the antibody fragments. In embodiments, the method further includes post-translational modification profiling of the antibody of interest. In embodiments, the method further includes post-translational modification mapping of post-translational modification hotspots by reduced peptide mapping LC-MS/MS analysis.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

The following examples are provided to illustrate particular features of certain embodiments. However, the particular features described below should not be considered as limitations on the scope of the invention, but rather as examples from which equivalents will be recognized by those of ordinary skill in the art.

Example

The following example is put forth so as to provide those of ordinary skill in the art with a complete disclosure and description of how to make and use the methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

High-Throughput Analysis of Antibody Charge Heterogeneity by Native Microfluidic Capillary Electrophoresis-Mass Spectrometry Develop a high-resolution, high-sensitivity and high-throughput native capillary electrophoresis (CE)-mass spectrometry (MS) method for antibody charge heterogeneity analysis.

A model mAb from NIST is used for a forced degradation study. Samples with different incubation times are cleaved by IdeS digestion to generate $F(ab')_2$ or Fc associated subunit species. The intact control and stressed antibodies are analyzed by Zipchip CE-MS at near native states for the identification of charge variants. The elevated charge variants are allocated to $F(ab')_2$ or Fc by the subunit charge variant analysis. The PTM hotspots are monitored by reduced peptide mapping LC-MS/MS analysis. Intact mass data is processed by PMi-Intact software. Reduced peptide mapping data is processed by BioPharma Finder 3.0 and Skyline-daily 4.2 for PTMs identification and quantification, respectively. A NIST antibody was used for thorough native Zipchip CE-MS system evaluation. The results showed zero carryover and good run-to-run reproducibility. High sensitivity measurement was achieved with 1 ng antibody loading amount. Acidic and basic charge variants were well separated from the main peak for the NIST antibody standard by Zipchip CE running at native conditions. The MS analysis identified two basic variants corresponding to the antibody with 1 and 2 unprocessed C-terminal lysines on the heavy chain, while an acidic variant was mainly caused by deamidation. Comparable and high-resolution charge variant separation was achieved between IEX and native CE-MS using the NIST antibody.

The NIST mAb reference standard and its heat-stressed forms were analyzed following incubation at 45° C. for up to 28 days. After incubation, samples were first cleaved by IdeS digestion to generate F(ab')2 and Fc fragments. The intact mass analysis of both control and stressed antibodies was conducted using a universal native Zipchip CE-MS method. The PTM hotspots were identified by reduced peptide mapping LC-MS/MS analysis to elucidate the elevated charge variants under stressed condition. A panel of fifteen antibodies, including IgG1, IgG4 and bispecific mAbs, were analyzed using the native Zipchip CE-MS method.

Sample Preparation

Forced degradation study: NIST IgG1 mAb (5 mg/mL, pH 6.0) was incubated at 45° C. for 0, 1, 4, 8, 15 and 28 days.

IdeS treatment: Each NIST mAb sample was diluted to 2 mg/mL with Milli-Q water. Then 125 units of IdeS (Promega) was added to 100 μg of mAb at enzyme/antibody ratio of 1.25/1. The mixture was incubated at 37° C. with shaking at 600 rpm for 30 minutes to generate F(ab')2 and Fc fragments. Control and stressed samples after each study/treatment were stored immediately at −20° C.

Native ZipChip CE-MS

The intact mass analysis of antibody and its charge variants was conducted using Zipchip CE interface (908 Devices) coupled to Exactive Plus EMR Obitrap mass spectrometer (Thermo Scientific). Antibody charge variants were separated on Native microfluidic HRN chip (22 cm separation channel, 908 Devices) with Native background electrolyte (BGE), pH~5.5 (908 Devices).

CE Parameters: Field strength: 650 V/cm, Pressure Assist: enabled, Pressure Assist Start Time: 0.2 mins, Replicate Delay: 30 sec, Injection volume: 1 nL MS Parameters (1) ESI Tune: Spray voltage: 0, Capillary temperature: 300° C., S-lens: 150, Sheath gas: 2, Aux gas: 0, trapping gas: 1.0.
(2) Acquisition method: Full scan analysis with positive mode detection, In-source CIS: 100 eV, Resolution: 17,500, AGC: 3e6, Max IT: 50 ms, Microscans: 3, Scan range: 1000-10000 m/z.

Strong Cation Exchange Chromatography (SCX)

Antibody charge variants were separated on MabPac SCX-10 column (4×250 mm) with pH gradient using CX-1 pH buffer (A: 5.6, B:10.2) (Thermo Fisher Scientific) on Agilent 1290 Infinity HPLC. Absorbance was measured at UV wavelength of 280 nm.

Data Processing

The intact mass data was deconvoluted using PMI-Intact software (Protein Metrics).

Results

A highly sensitive and universal 12-min method using native ZipChip CE-MS has been developed and applied for the charge variant analysis of IgG1, IgG4 and bispecific IgG4 antibodies. Comparable charge variant separation was obtained between native ZipChip CE-MS and SCX methods. The resolved charge variants were identified by native MS analysis. Antibodies with close pI values can be separated well. Co-migrated antibodies were identified individually based on simplified native mass spectrum. Increased levels of acidic variants and Fab fragments resulting from incubation under the stressed condition were localized within the F(ab')2 and Fc domains by subunit analysis. Furthermore, higher resolution subunit analysis revealed an additional acid variant introduced from isomerization and increased half glycosylated species under stressed condition.

Comparable Separation of Antibody Charge Variants between CE-MS and SCX-UV

Figure 2A:
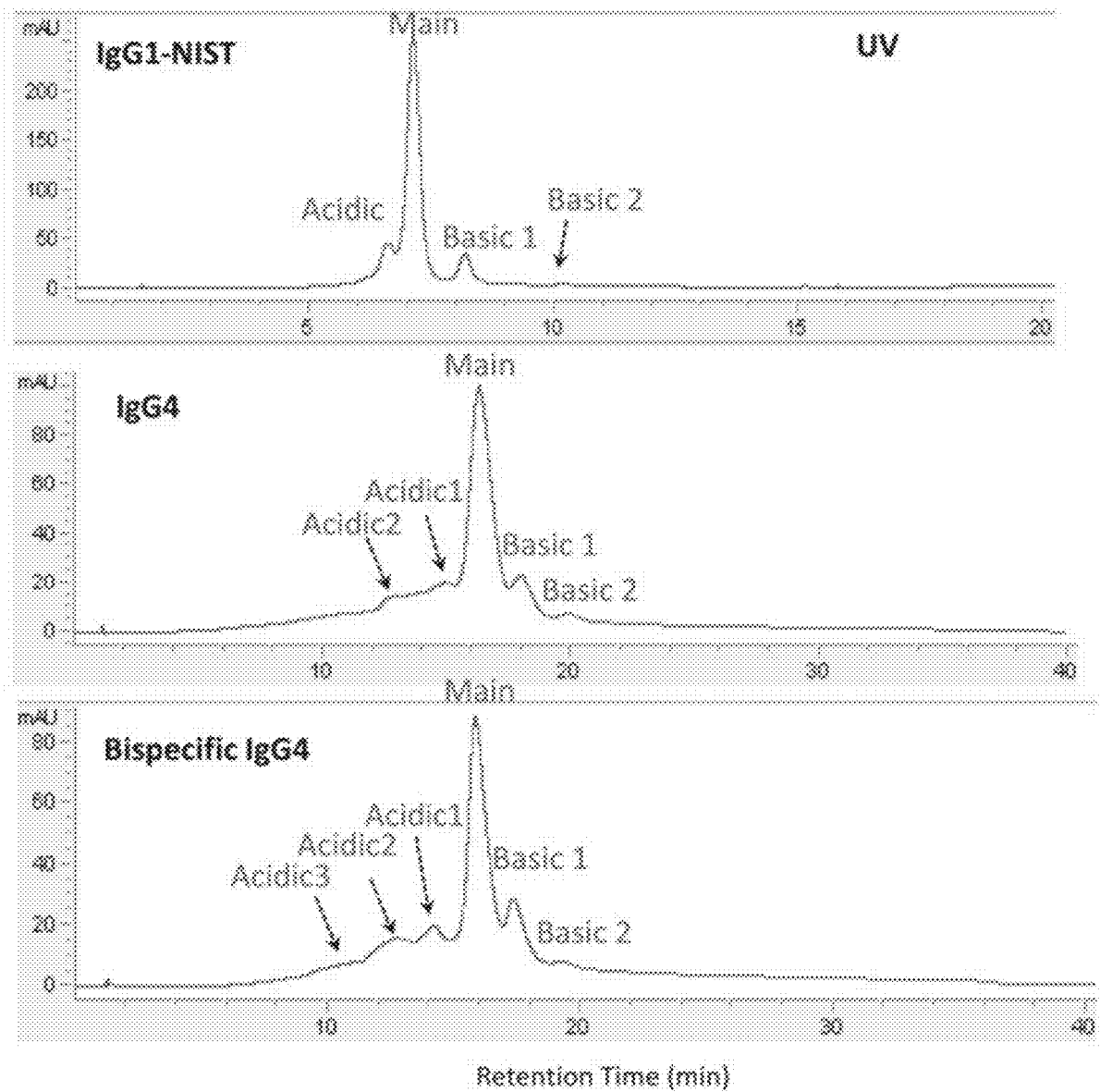
FIGS. 2A and 2B are a set of traces showing comparable separation of antibody charge variants between CE-MS (FIG. 2A) and SCX-UV (FIG. 2B).
Figure 2B:
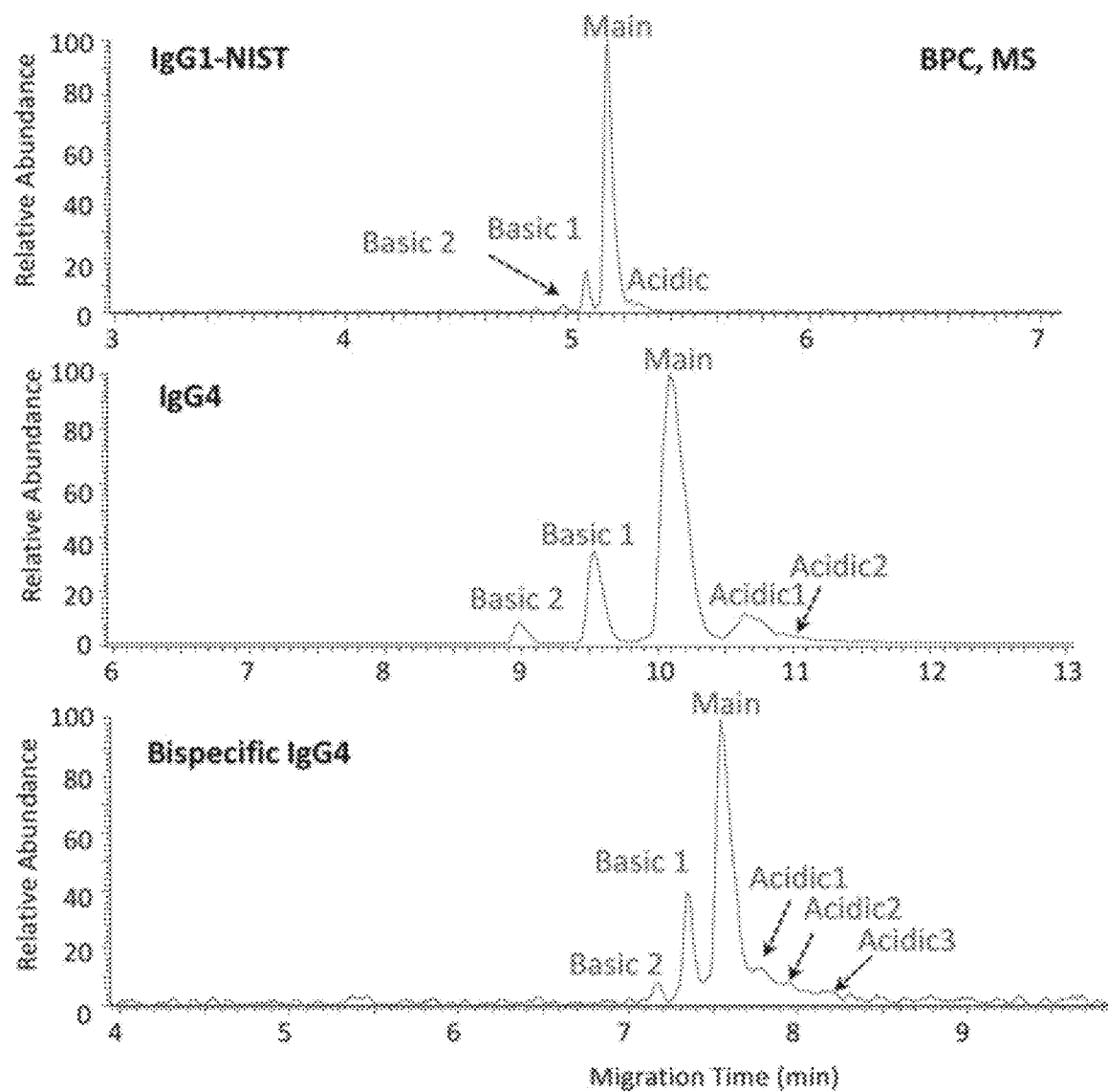

Three antibody standards including IgG1, IgG4 and Bispecific IgG4 were analyzed by high resolution SCX-UV and Native ZipChip CE-MS. Identical charge variant separation profiles were obtained between two platforms (FIG. 2A-2B).

Sensitivity and Carryover Tests of Native ZipChip CE-MS

Figure 3A:
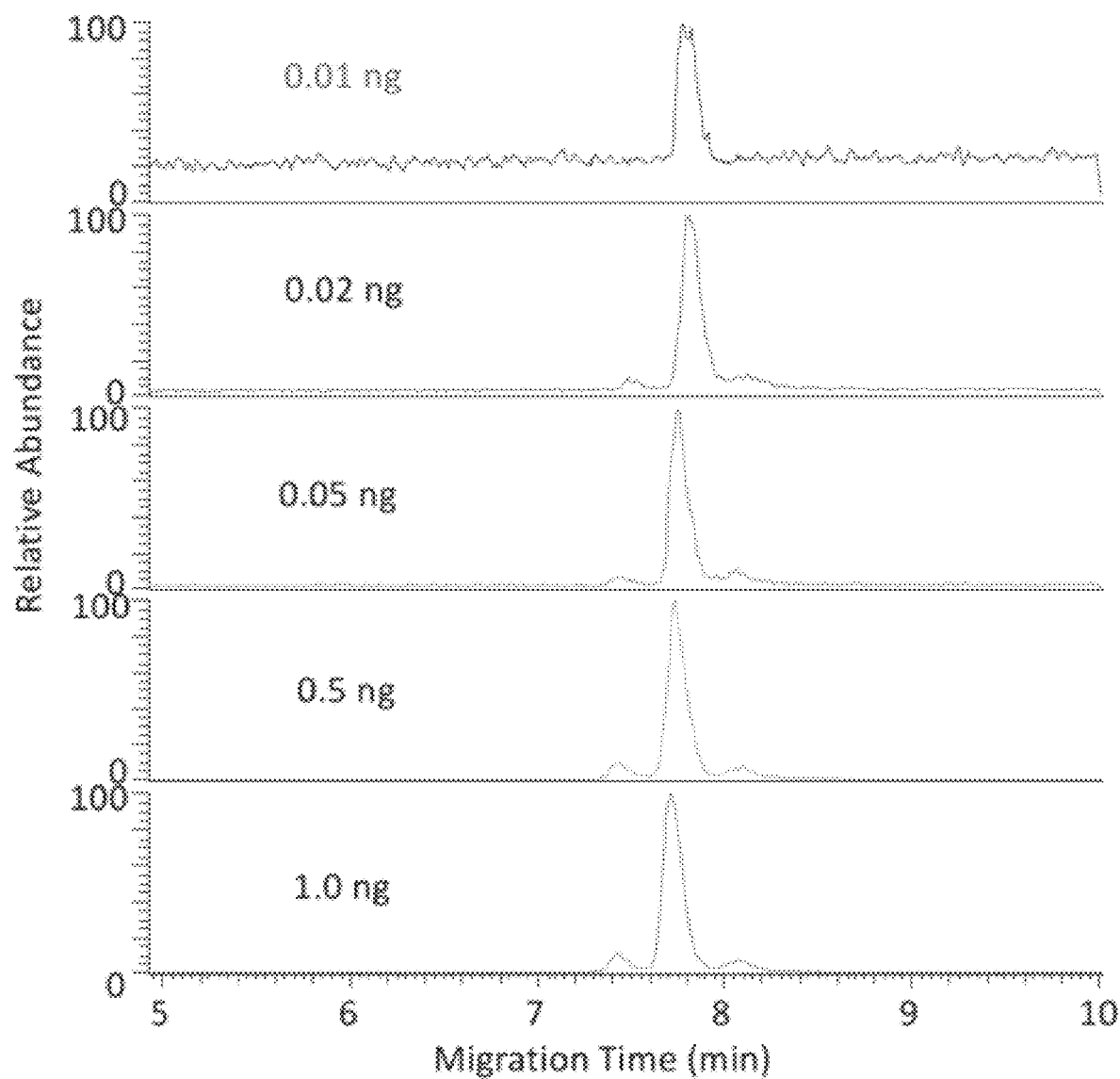
FIGS. 3A-3C are a set of graphs showing sensitivity and carryover tests of native ZipChip CE-MS. Sensitivity of IgG1 (FIG. 3A), IgG4 (FIG. 3B) and Zero Carryover (FIG. 3C) of Native ZipChip CE.
Figure 3B:
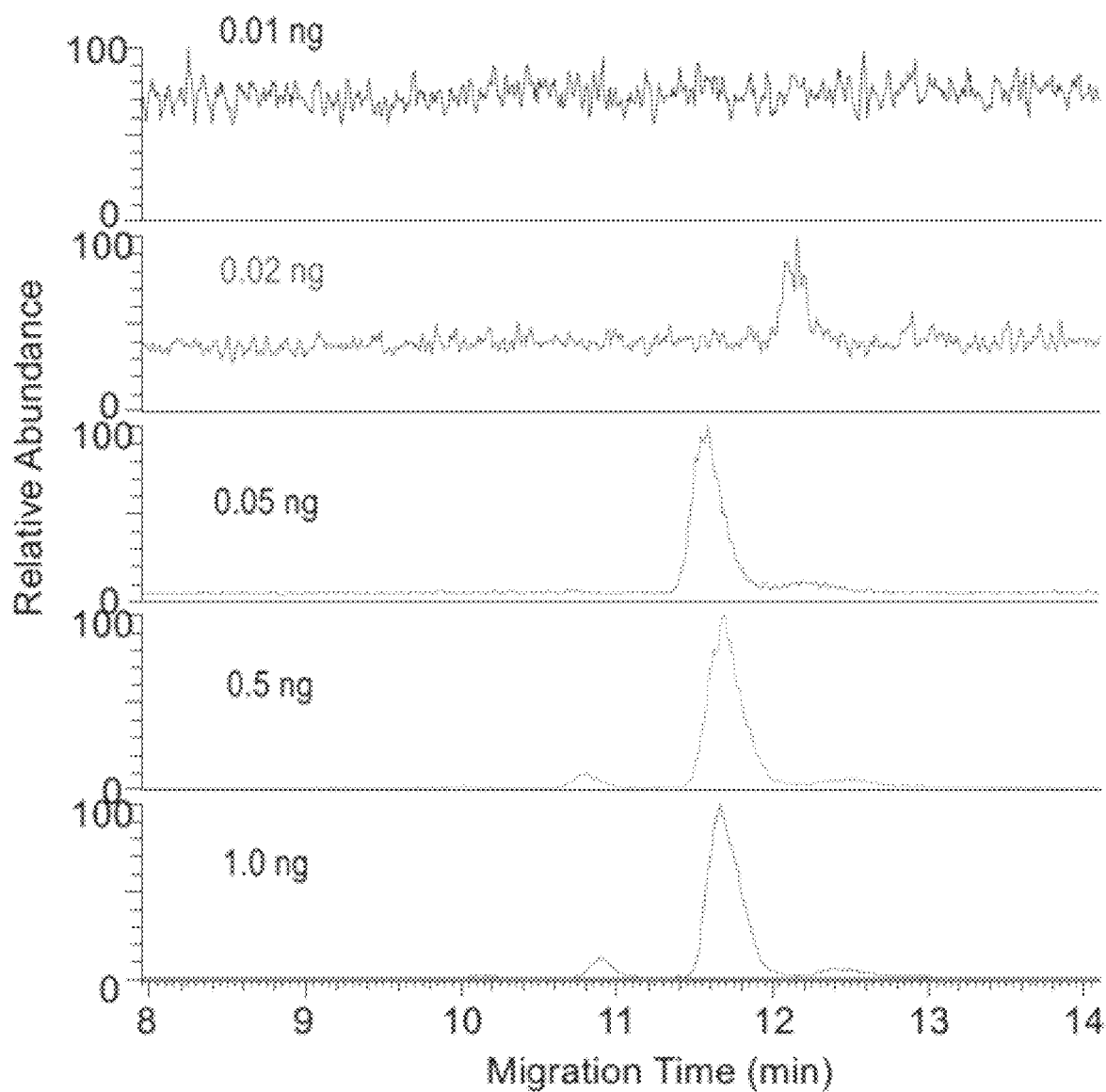
Figure 3C:
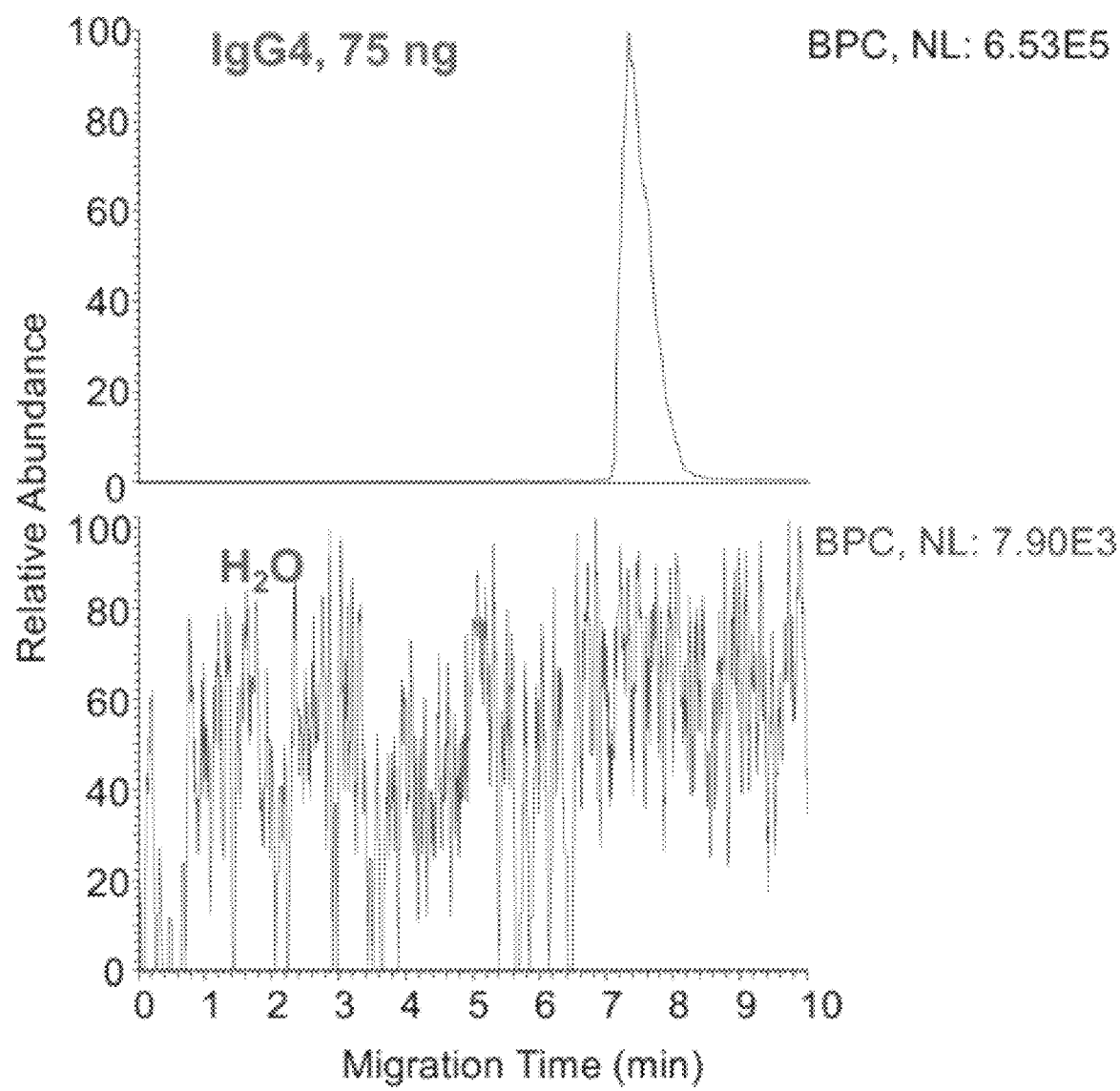

The ZipChip CE-MS combined with nanospray ESI provides great sensitivity of detecting low abundant species. IgG1 and IgG4 were detected at 0.01 ng and 0.02 ng, respectively. No carryover was observed from run-to-run injections (FIGS. 3A-3C).

Charge Variant Analysis of Intact Antibody

Figure 4:
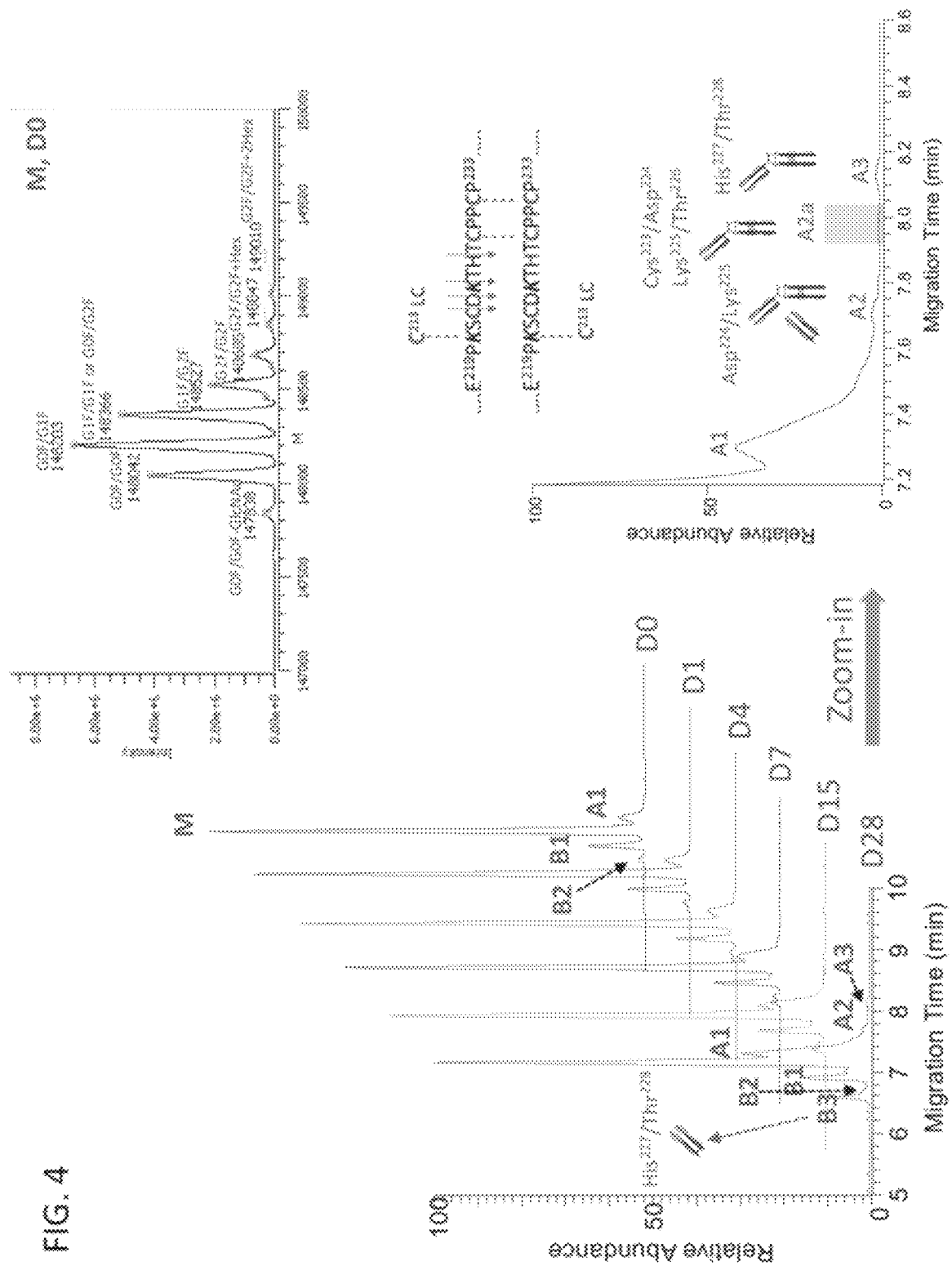
FIG. 4 is a set of graphs showing the charge variant separation of intact NIST mAb and SEQ ID NO: 1.

Intact control and heat (45° C.) stressed NIST mAbs were analyzed by native ZipChip CE-MS. Deconvoluted mass data indicated that 4 major Fab cleavages at the upper hinge region of NIST mAb were generated upon 28-day heat stress, in addition to significantly increased acidic variant (A1) compared to the control (FIG. 4 and Table 2).

TABLE 2

Summary of Charge Variant Identification

| Charge Variants | Control NIST mAb | Stressed NIST mAb (45° C., pH 6.0, 28 days) |
|---|---|---|
| Basic 1 (B1) | +1 C-terminal lysine | +1 C-terminal lysine |
| Basic 2 (B2) | +2 C-terminal lysine | +2 C-terminal lysine |
| Basic 3 (B3) | ND | Fab cleavage at $His^{227}/Thr^{228}$ |
| Acidic 1 (A1) | +Deamidation | +Deamidation |
| Acidic 2 (A2) | ND | Fab cleavage at $Asp^{224}/Lys^{225}$ |
| Acidic 2a (A2a) | ND | Loss of Fab cleaved at $Cys^{223}/Asp^{224}$ and $Lys^{225}/Thr^{226}$ |
| Acidic 3 (A3) | ND | Loss of Fab cleaved at $His^{227}/Thr^{228}$ |

Note:
ND—not detected

Charge Variant Analysis of Antibody F(ab')2 and Fc Subunits

Figure 5A:
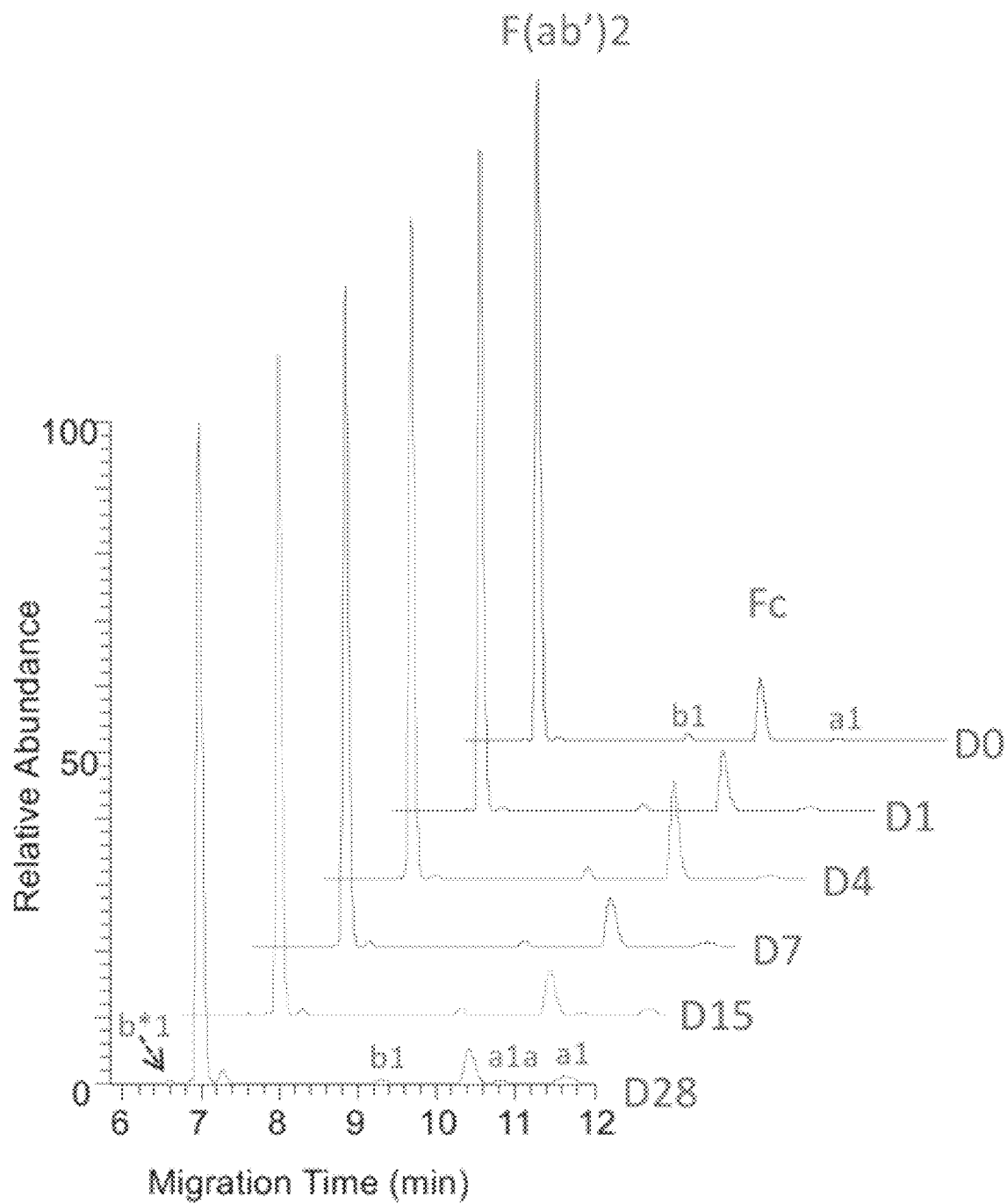
FIGS. 5A-5C are a set of traces showing the charge variant analysis of antibody F(ab')2 and Fc subunits. The charge variant separation of (FIG. 5A) IdeS treated control and stressed NIST mAbs, Zoom-in Electropherograms of F(ab')2 (FIG. 5B) and Fc (FIG. 5C) regions.
Figure 5B:
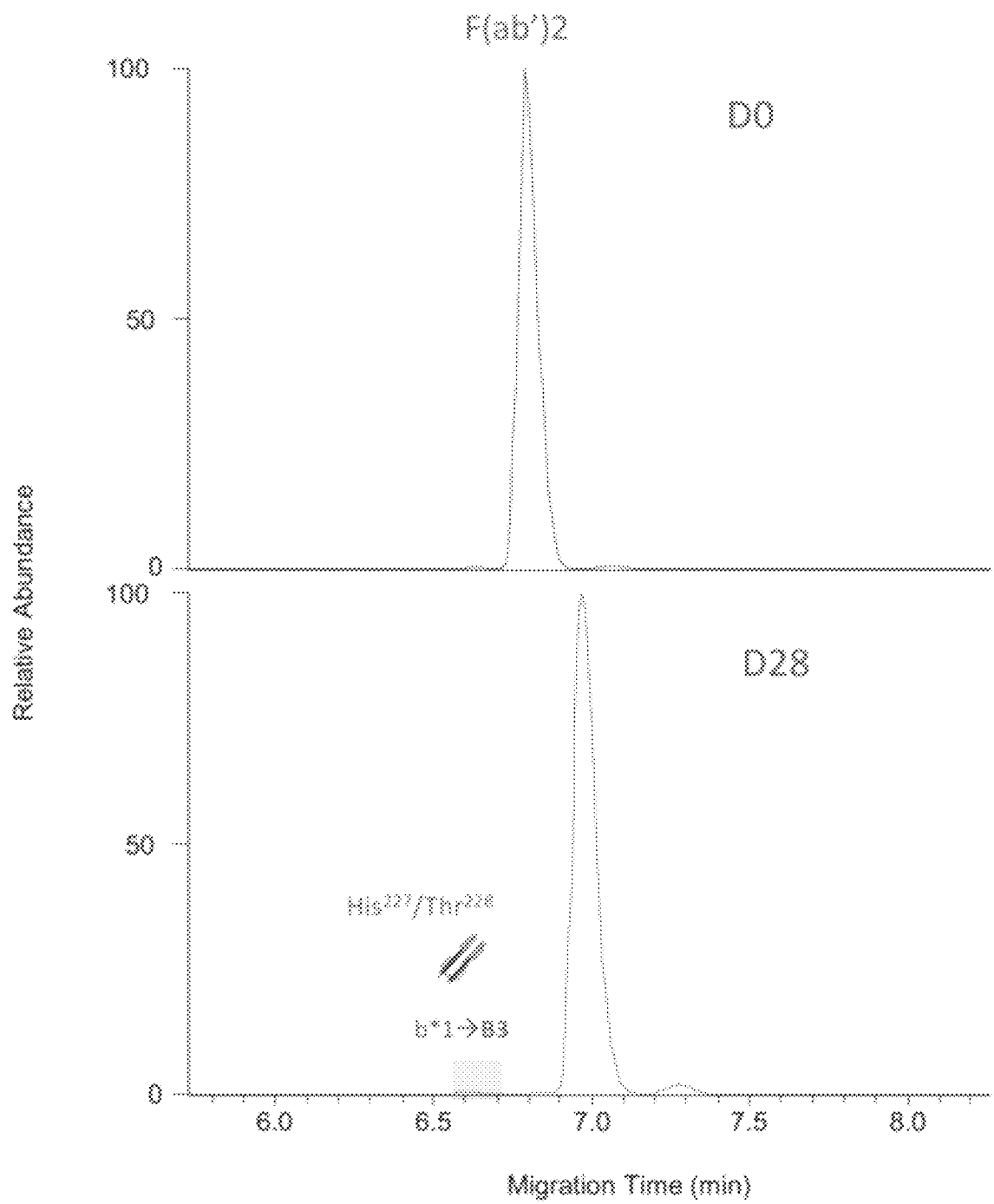
Figure 5C:
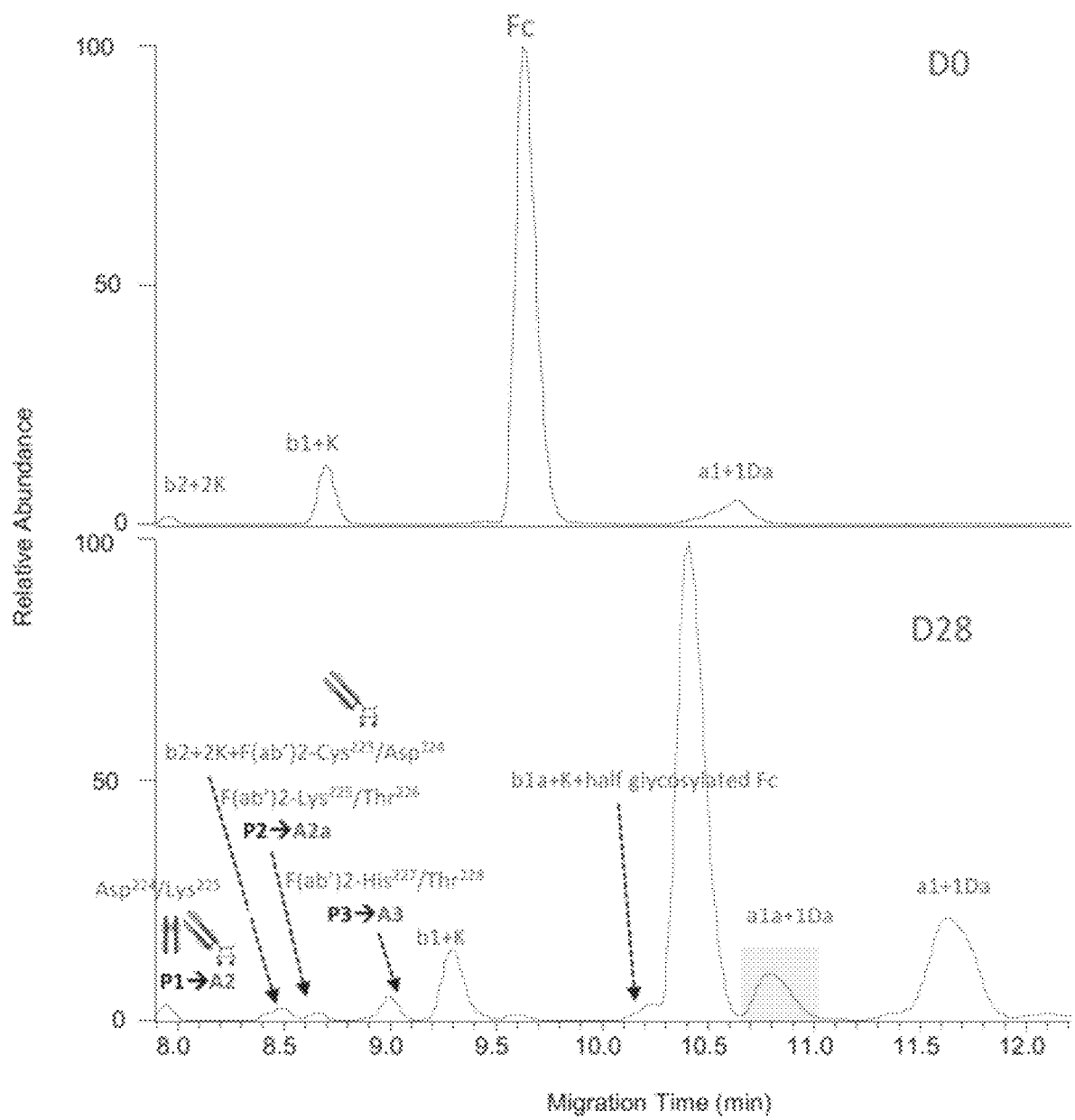

F(ab')2 and Fc were well separated by the universal CE-MS method. All minor peaks were identified and shown in FIGS. 5A-5C. New charge variants resulting from 28-day incubation were shown in blue highlight regions. Two basic variants with 1 and 2 unprocessed C-terminal lysine were located on Fc region (FIG. 5C). The basic variant 3, resulting from Fab cleavage at $His^{227}/Thr^{228}$ in stressed sample (45° C., D28), was identified as F(ab')2 basic variant (b*1) in FIG. 5B.

All other Fab cleavage sites were found in the acid region of F(ab')2 and in the same order as those were identified during intact antibody analysis. For Fc acidic region, a new acidic variant A1a due to Asp isomerization showed up in D28 sample. Compared to main Fc, the +1 Da mass increase of both a1 and a1a indicated that the acidic variant might be caused by deamidation. This was confirmed by peptide mapping result shown in Table 3.

TABLE 3

Summary of Major PTMs Showing Difference under Stressed Conditions

| Antibody Region | PTMs | Site | D 0 (Control) | D 1 | D 4 | D 7 | D 15 | D 28 |
|---|---|---|---|---|---|---|---|---|
| Fc | Deamidation | HC Asn387 | 1.61% | 1.64% | 1.71% | 1.91% | 2.15% | 2.64% |
|  | Deamidation | HC Asn392 | 0.75% | 0.83% | 1.04% | 1.40% | 1.99% | 3.03% |
|  | Oxidation | HC Met255 | 1.23% | 1.56% | 1.66% | 1.88% | 2.05% | 3.00% |
|  | Isomerization | HC Asp283 | 0.65% | 0.70% | 0.87% | 1.29% | 1.70% | 2.81% |
| F(ab')2 | Isomerization | LC Asp166 | 2.65% | 3.28% | 3.58% | 4.64% | 5.59% | 7.62% |

Separation of Antibody Mixtures for High-throughput Intact Mass Analysis

Figure 6A:
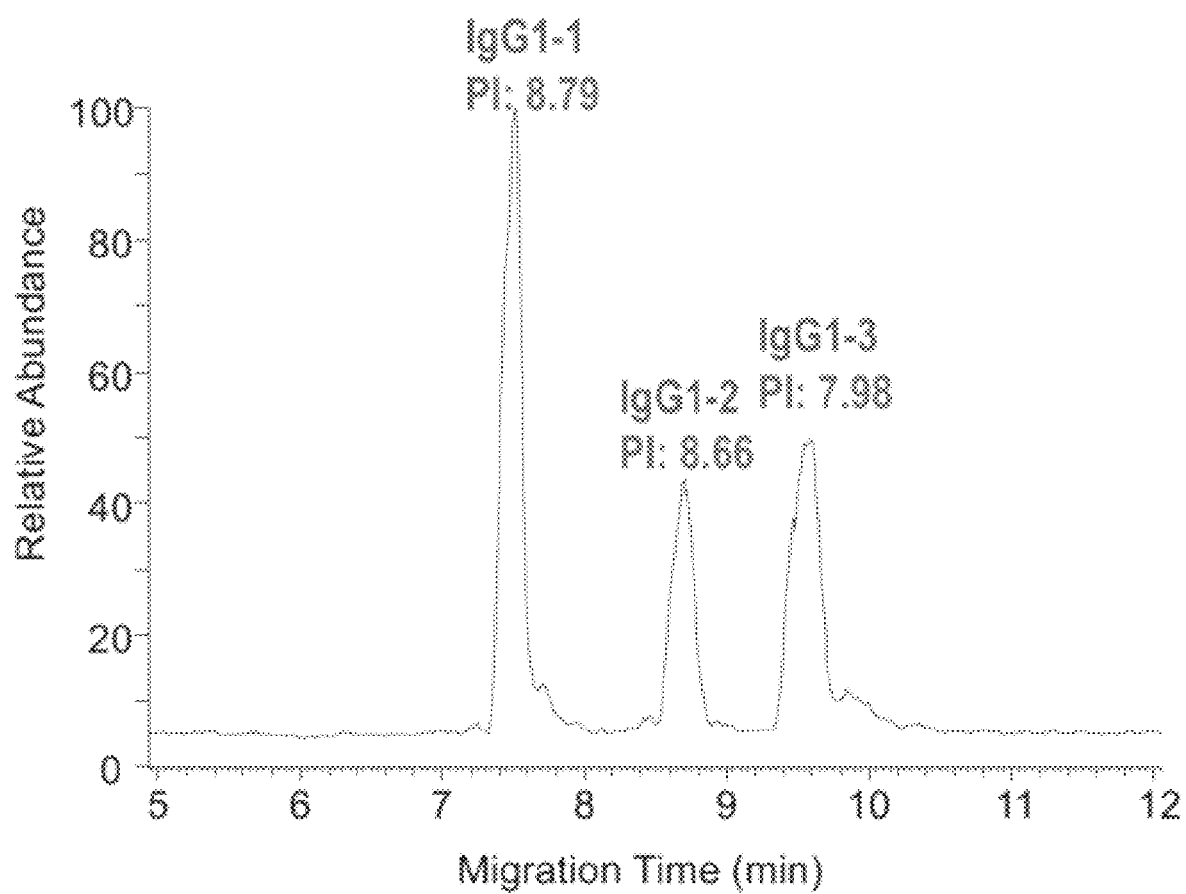
FIGS. 6A-6E are a set of graphs showing the separation of 3 IgG1 mAbs (FIG. 6A), 5 Bispecific IgG4 mAbs (FIG. 6B), 10 mAbs (FIG. 6C) and Identification of co-migrated mAbs (FIGS. 6D and 6E) by Native ZipChip CE-MS.
Figure 6B:
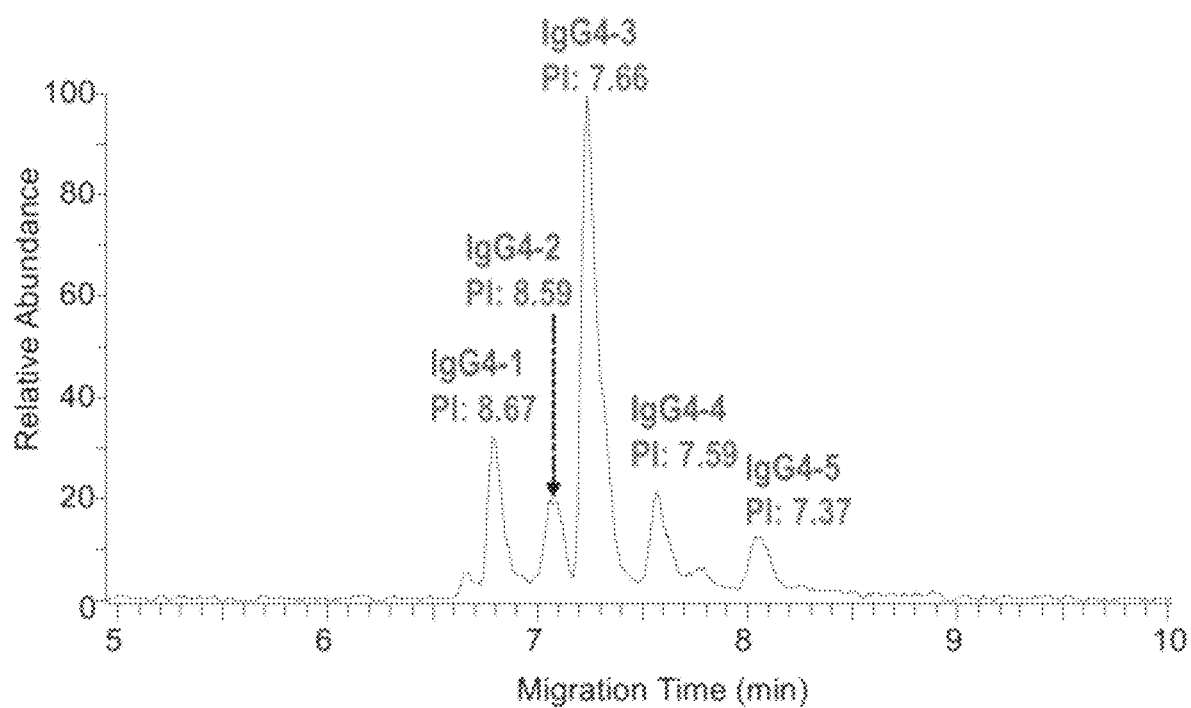
Figure 6C:
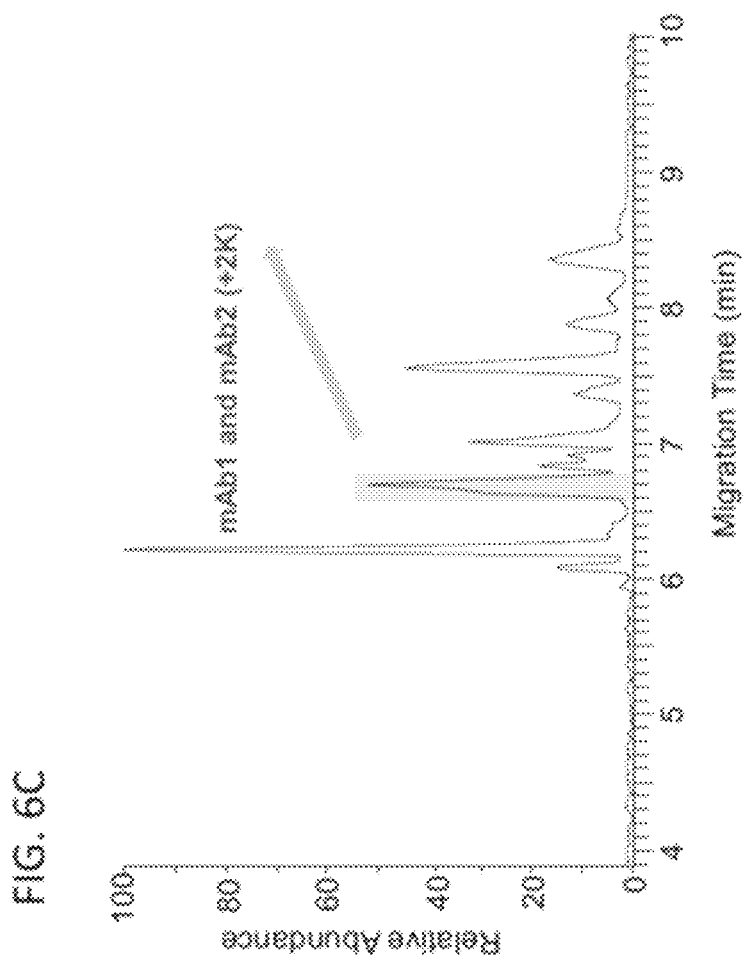
Figure 6D:
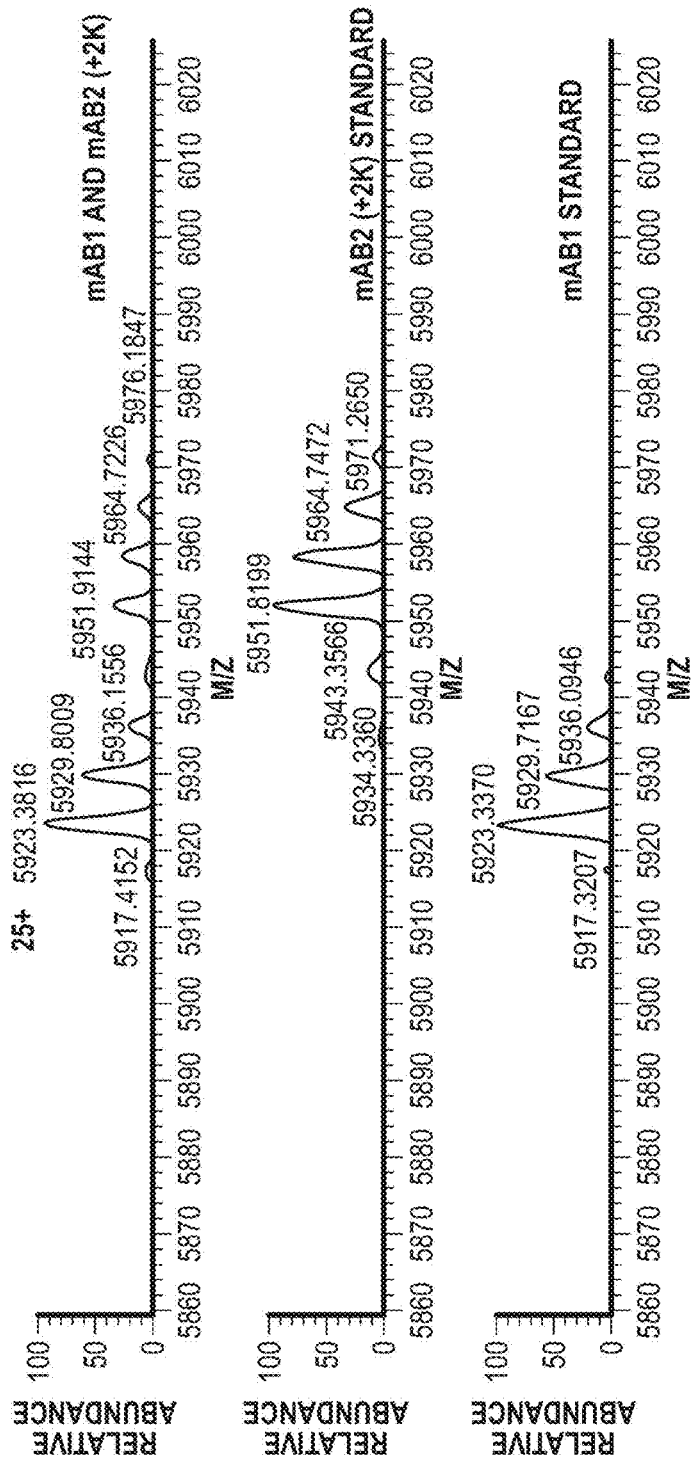
Figure 6E:
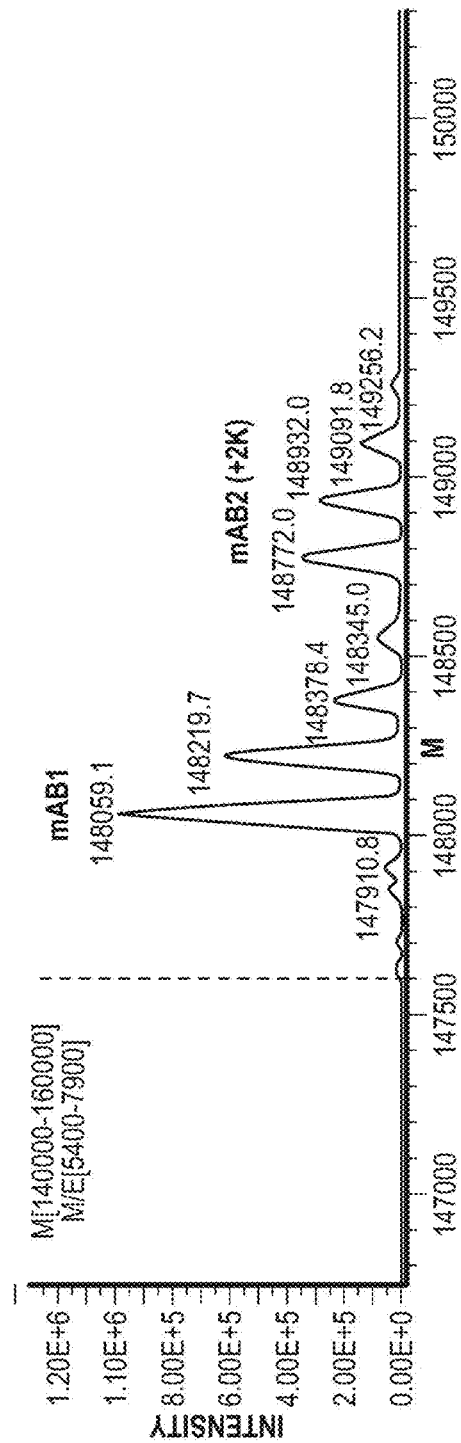

Three IgG1 mAbs in mixture1 (FIG. 6A) and five IgG4 bispecific mAbs in mixture2 (FIG. 6B) were well separated, which can be applied for intact mass analysis of co-formulated drugs. Even if two antibodies co-migrated together (blue highlight in FIG. 6C), those can be identified individually from native MS data (FIGS. 6D and 6E), see FIG. 6E for convoluted spectra.

Besides high-resolution charge variant analysis of a single antibody, the native ZipChip CE-MS method can also be used as a high-throughput and high-sensitivity approach for intact mass analysis of antibody mixture and ADCs.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for detecting and/or discriminating between post-translational modification variants of an antibody of interest in a sample, comprising:
   (a) subjecting a sample comprising one or more antibodies of interest to thermal stress to form a stressed sample;
   (b) contacting said stressed sample with a protease to digest the sample into antibody fragments, wherein said antibody fragments comprise F(ab')$_2$ fragments and Fc fragments;
   (c) separating said antibody fragments by molecular weight and/or charge in one or more capillaries using capillary electrophoresis under native conditions, wherein said capillary electrophoresis is in an integrated microfluidic platform and said native conditions preserve said F(ab')$_2$ fragments and said Fc fragments;
   (d) eluting separated antibody fragments from the one or more capillaries; and
   (e) determining the mass of the eluted antibody fragments by mass spectrometry analysis, thereby detecting and/or discriminating between post-translational modification variants of the antibody of interest,
   wherein said capillary electrophoresis is coupled online to said mass spectrometer.

2. The method of claim 1, wherein the post-translational modification comprises one or more of deamidation, oxidation, glycation, disulfide formation, N-terminal pyroglutamate formation, C-terminal lysine removal, and high mannose glycosylation.

3. The method of claim 1, wherein the protease comprises IdeS.

4. The method of claim 1, wherein the antibody of interest is a monoclonal antibody.

5. The method of claim 1, wherein the antibody fragments are separated by charge and the method is a method of detecting and/or discriminating between charge variants of the antibody of interest.

6. The method of claim 1, wherein the antibody fragments are separated by molecular weight and the method is a method of detecting and/or discriminating between size variants of the antibody of interest.

7. The method of claim 1, further comprising determining a relative or absolute amount of the post-translational modification variants of an antibody of interest in a sample.

8. The method of claim 1, wherein the antibody of interest comprises a bispecific antibody.

9. The method of claim 1, wherein the sample includes an internal standard.

10. The method of claim 1, wherein the one or more capillaries comprise a separation matrix.

11. The method of claim 10, wherein the separating comprises a sieving matrix configured to separate proteins by molecular weight.

12. The method of claim 1, wherein subjecting said sample to thermal stress comprises incubating said sample at about 45° C. for about 1, 4, 8, 15, or 28 days.

13. The method of claim 1, further comprising identifying the antibody fragments.

14. The method of claim 1, further comprising identifying the post-translational modification present on the antibody fragments.

15. The method of claim 1, wherein the antibody of interest is of isotype IgG1, IgG2, IgG3, IgG4, or mixed isotype.

16. The method of claim 1, further comprising post-translational modification profiling of the antibody of interest.

17. The method of claim 1, further comprising post-translational modification mapping of post-translational modification hotspots by reduced peptide mapping LC-MS/MS analysis.

18. The method of claim 1, wherein the sample comprises a mixture of antibodies of interest.

19. The method of claim 1, wherein the antibody of interest is an antibody drug conjugate.

20. A method for detecting and/or discriminating between post-translational modification variants of an antibody of interest in a sample, comprising:
   (a) incubating a sample comprising one or more antibodies of interest at about 45° C. for from 0 to 28 days to form a stressed sample;
   (b) contacting said stressed sample with an IdeS protease to digest the sample into antibody fragments, wherein the protease to sample ratio is about 1.25 units of protease to about 1 μg sample and said antibody fragments comprise F(ab')$_2$ fragments and Fc fragments;
   (c) separating said antibody fragments by molecular weight and/or charge in one or more capillaries comprising a sieving matrix using capillary electrophoresis under native conditions, wherein said capillary electrophoresis is in an integrated microfluidic platform and said native conditions preserve said F(ab')$_2$ fragments and said Fc fragments;
   (d) eluting separated antibody fragments from the one or more capillaries; and
   (e) determining the mass of the eluted antibody fragments by mass spectrometry analysis, thereby detecting and/ or discriminating between post-translational modification variants of the antibody of interest,
wherein said capillary electrophoresis is coupled online to said mass spectrometer.

* * * * *

UNITED STATES PATENT AND TRADEMARK OFFICE
CERTIFICATE OF CORRECTION

PATENT NO. : 12,169,203 B2  
APPLICATION NO. : 16/777230  
DATED : December 17, 2024  
INVENTOR(S) : Hongxia Wang, Haibo Qiu and Ning Li Page 1 of 1

It is certified that error appears in the above-identified patent and that said Letters Patent is hereby corrected as shown below:

On the Title Page

Column 2, item (56) under Other Publications, Line 8, delete "168e176" and insert -- 168-176 --.

Signed and Sealed this  
Eleventh Day of March, 2025

Coke Morgan Stewart  
*Acting Director of the United States Patent and Trademark Office*